United States Patent [19]

Nicola et al.

[11] Patent Number: 5,525,628

[45] Date of Patent: Jun. 11, 1996

[54] SALTS OF A GLUTATHIONE ALKYLESTER AND AN AMINOACIDS

[75] Inventors: Massimo Nicola, Pavia; Marco Inglesi; Giancarlo B. Fregnan, both of Milan; Guido Vandoni, Correzzana, all of Italy

[73] Assignee: Edmond Pharma S.R.L., Milan, Italy

[21] Appl. No.: 193,140

[22] PCT Filed: Jun. 9, 1993

[86] PCT No.: PCT/EP93/01462

§ 371 Date: Nov. 28, 1994

§ 102(e) Date: Nov. 28, 1994

[87] PCT Pub. No.: WO93/25573

PCT Pub. Date: Dec. 23, 1993

[30] Foreign Application Priority Data

Jun. 12, 1992 [IT] Italy ...................... MI92A1445

[51] Int. Cl.$^6$ ............................................. A61K 31/195
[52] U.S. Cl. ........................ 514/562; 560/151; 560/147
[58] Field of Search ...................... 560/147, 151; 514/562

[56] References Cited

FOREIGN PATENT DOCUMENTS

| 0249401 | 12/1987 | European Pat. Off. . |
| 498089 | 10/1970 | Switzerland . |
| 1110392 | 1/1966 | United Kingdom . |

*Primary Examiner*—José G. Dees
*Assistant Examiner*—Samuel Barts
*Attorney, Agent, or Firm*—Michael N. Meller

[57] ABSTRACT

Crystalline non-hygroscopic salt of glutathione alkylester of the formula (I)

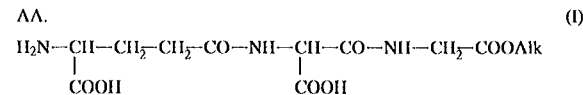

wherein AA is an amino acid are disclosed.

4 Claims, No Drawings

SALTS OF A GLUTATHIONE ALKYLESTER AND AN AMINOACIDS

This application is filed under U.S.C. 371 of the application PCT/EP 93101462 filed 6/9/93.

The present invention concerns new salts of the L-γ-glutamyl-L-cysteinyl alkyl esters.

More particularly, the invention relates to the salts with amino acids of glutathione ($C_1$–$C_6$) alkylesters and to their solvates. The invention further relates to a process for the preparation of these new salts and to pharmaceutical compositions containing such salts as active ingredient.

Glutathione, L-γ-glutamyl-L-cysteinylglycine or GSH, is represented by the formula (A)

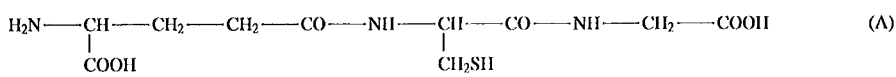

Glutathione, a tripeptide containing an SH group, is well known as a cellular reducer, as a catalyst in a great number of biological reactions, as a metabolic reagent, and as a form of cysteine storage and control.

Glutathione plays a very important role in cell protection against free radicals, against reactive oxygenated species such as hydroperoxides and peroxides, and against toxic compounds of either endogenous and hexogenous origin (A. Meister et al., Ann. Rev. Biochen 52,711,1983).

An increase of intracellular GSH may therefore induce cell protection against damage due to radiation, or to toxic chemical species, such as endogenous peroxides or highly toxic drugs.

Glutathione as such, however, cannot pass the cellular barrier and consequently does not enter cells, while its esters do. More particularly its ethylester (GSEt) is capable of penetrating the cells, thus undergoing in situ hydrolization (M. E. Anderson et al. Arch. Biochem. Biophys. 1985,239, 538–538; U.S. Pat. No. 170,489).

Glutathione ethylester (on glycine) is prepared according to the method described in the publication by M. E. Anderson et al. mentioned above, but the final product always contains a certain amount of diester (on both glutamic acid and glycine) which must be eliminated as it is toxic.

This impurity can be removed by chromatography on weak cation exchange resin columns, as described in U.S. Pat. 4,710,489, but such an operation is not easy, when it has to be performed on an industrial scale.

U.S. Pat. No. 4,709,013 describes glutathione ester sulphates highly crystallizable and therefore easily purifiable, allowing their easy transformation into glutathione monoester devoid of the toxic diester.

Although the sulphates described in the above document are crystallizable, the thus obtained crystals are hygroscopic. The usefulness of such sulphates is therefore limited to their use as intermediates in the purification of glutathione esters.

Consequently, these sulphates cannot be used as active ingredients of pharmaceutical compositions, due to the difficulties encountered in their handling in pharmaceutical technique.

Another reason which hinders said sulphates from being used as medicaments is their high acidity.

Patent EP 257 992 describes the use of glutathione monoesters for the preparation of agents suitable for use in the prophylaxis and treatment of cerebral ischemia and, as active ingredients, it reports also inorganic salts such as hydrochlorides, nitrates, or organic ones such as oxalates, p-toluensulphonates, maleates, etc. In the above document it is however pointed out that when such monoesters are being administered in the form of salts, they are previously desalted, or administered by concurrent addition of a base, i.e. sodium carbonate, neutralizing them. Consequently, glutathione esters stable crystalline salts directly useful as active ingredients for pharmaceutical compositions are not known in literature.

It has now surprisingly been found that glutathione monoalkylesters, namely the esters of a tripeptide with an initial alpha-aminoacid unit, easily yield salts with other aminoacids.

Moreover, it has been found that these salts with aminoacids are crystalline and not hygroscopic.

Finally, it has been found that the above reported crystalline non hygroscopic salts of glutathione alkylesters are even pharmacologically more active that the free base, and are easy to handle in pharmaceutical technique for the preparation of compositions for therapeutic use.

Thus, it is an object of the present invention to provide crystalline non hygroscopic salts of glutathione alkylesters (GSAlk) with aminoacids of formula (I)

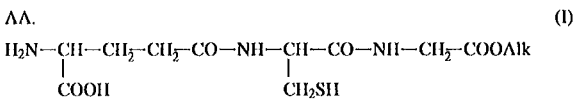

wherein AA is the salifying aminoacid and Alk represents an alkyl group containing from 1 to 6 carbon atoms such as methyl, ethyl, propyl, isopropyl, n-butyl, isobutyl, n-pentyl, isoamyl, n-hexyl.

Advantageous salts of glutathione alkylesters are those of glutathione ethylester (GSTt) represented by the formula (I')

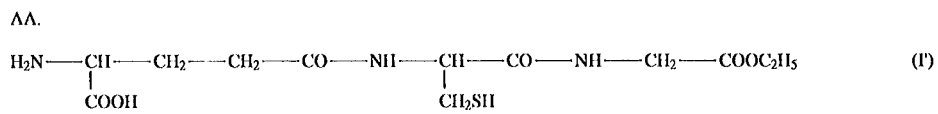

wherein AA is as defined above, and those of glutathione isopropyl ester (GSIpr) represented by the formula (I")

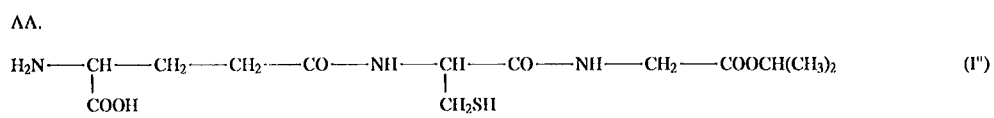

wherein AA is as defined above.

There are mentioned, among the salifying aminoacids giving crystalline non hygroscopic salts, natural alpha-aminoacids such as glycine, alanine, aspartic acid and glutamic acid, but other salifying aminoacids such as pyroglutamic acid, γ-aminobutyric acid and taurine also provide considerable advantages.

As compared with sulphate and hydrochloride, namely with the salts specifically described in literature, the new GSAlk salts of the present invention, besides the advantage of being crystalline, stable and not hygroscopic, they have also the advantage of being physiologically compatible, being less acid. In fact, in aqueous solution, they provide a physiologically acceptable pll.

In this connection, particularly preferred GSAlk according to the present invention are those having the formula (I) above, in which AA is selected from the group consisting of taurine, γ-aminobutyric acid, pyroglutamic acid, glycine, alanine, aspartic acid and glutamic acid and Alk is ethyl (formula I' above) or isopropyl (formula I" above).

Moreover, while the GSEt sulphate described in U.S. Pat. No. 4,709,013 crystallizes with some difficulty and in a modest yield, the salts of the present invention are easily prepared by precipitation and are obtained in extremely high yields.

Thus, according to another of its aspects, the present invention concerns a process for the preparation of crystalline non hygroscopic salts of glutathione alkylester (I). which comprises:

a) treating said glutathione alkylester with the adequate aminoacid in water b) evaporating the solvent under reduced pressure till a small volume c) treating the reaction mixture with an alcohol and isolating the precipitated salt.

Salification is carried out at a temperature ranging from 0° to 40° C., during a period of time varying from 1 to 6 hours, and ethyl alcohol is used by preference as the precipitating alcohol. The thus obtained salt is isolated by simple filtration of the precipitate. If necessary, said precipitate may be washed with cold ethyl alcohol or with another organic solvent.

The aminoacid which forms the GSAlk salt is preferably used in equimolecular amount in respect of the starting GSAlk.

The thus obtained new salts may contain some crystallization water of ethyl alcohol. Said solvates are within the scope of the present invention.

GSAlk salts and their solvates increase the stability and the solubility of GSAlk, thus increasing glutathione intracellular levels.

Consequently they are useful as therapeutically active agents in detoxication from drugs, in cellular protection versus peroxides, free radicals and radiations.

Besides, the compounds of the present invention may be used to prevent cellular damage due to ischemia and/or hypoxia.

Thus, it is another object of the present invention to provide pharmaceutical compositions containing as active ingredient, at least one of the crystalline non-hygroscopic salts of GSAlk with aminoacids or of their solvates in admixture with a pharmaceutical carrier.

The pharmaceutical compositions of the present invention contain from 10 to 1000 mg of active ingredient calculated on the basis of glutathione alkylester, by preference from 20 to 500 mg of equivalent in glutathione alkylester per dose unit They can be prepared in form of vials or tiny bottles for intravenous or intramuscular injection, as suppositories or rectal capsules, in forms for the oral administration, such as tablets, capsules or granulates, or as pharmaceutical form suitable for nasal adiministration in nebulizers.

The carriers are those of common use in pharmaceutical technique for preparing oral, parenteral, rectal, transdermal or intranasal formulations, provided they are chemically compatible with the active or inert ingredients.

The following non-limiting examples illustrate the invention.

EXAMPLE 1

GSEt taurine salt (compound 1)

Equimolar quantities of GSEt (4.8 g) and of taurine (1.81 g) were dissolved in $H_2O$ (80 ml) at room temperature. The solvent was evaporated to small volume in vacuum. The product was allowed to crystallize after adding 100 ml of ethyl alcohol. Filtration and washing with a small quantity of cold ethyl alcohol were done Drying in oven at 40° C. in vacuum was then performed, obtaining 5.91 g.

m.p.=140°–145° C.

Calculated: C=36.51; H=6.13; N=12.17. Found: C=36.55; H=6.12; N=12.20.

HPLC assay=73% (GSEt); 27% (Taurine)

EXAMPLE 2

GSEt γ-aminobutyric acid salt (compound 2)

Equimolar quantities of GSEt (4.8 g) and of γ-aminobutyric acid (1.49 g) were dissolved in $H_2O$ (60 ml) at room temperature. The solvent was evaporated to small volume, ethyl alcohol (100 ml) was added and the product was allowed to crystallize. Filtration and washing with cold ethyl alcohol were done. Drying in oven at 40° C. in vacuum was then performed, obtaining 5.85 g.

m.p.=124°–127° C.

Calculated: C=43.82; H=6.90; N=12.78. Found: C=43.79; H=6.89; N=12.80.

HPLC assay=76.48% (GSEt); 23.52% (γ-aminobutyric acid)

EXAMPLE 3

GSEt pyroglutamic acid salt (compound 3)

Equimolar quantities of GSEt (4.8 g) and of pyroglutamic acid (1.86 g) were dissolved in $H_2O$ (60 ml) at room temperature. The solvent was evaporated to small volume, ethyl alcohol (100 ml) was added and the product was allowed to crystallize. Filtration and washing with cold ethyl alcohol were done. Drying in oven at 40° C. in vacuum was then performed, obtaining 3.50 g.

m.p.=130°–133° C.

Calculated: C=43.96; H=6.07; N=12.06. Found: C=43.94; H=6.08; N=12.08.

HPLC assay=72.2% (GSEt); 27.8% (pyroglutamic acid)

EXAMPLE 4

GSEt glycine salt (compound 4)

Equimolar quantities of GSEt (4.8 g) and of glycine (1.07 g) were dissolved in $H_2O$ (70 ml) at room temperature. The solvent was evaporated to small volume, ethyl alcohol (100 ml) was added and the product was allowed to crystallize.

Filtration and washing with cold ethyl alcohol were done. Drying in oven at 40° C. in vacuum was then performed, obtaining 4.80 g.

m.p.=161°–164° C.

Calculated: C=40.97; H=6.38; N=13.65. Found: C=40.93; H=6.37; N=13.67.

HPLC assay=81.7% (GSEt); 18.3% (glycine)

EXAMPLE 5

GSEt alanine salt (compound 5)

Equimolar quantities of GSEt (4.8 g) and of alanine (1.27 g) were dissolved in $H_2O$ (70 ml) at room temperature. The solvent was evaporated to small volume, ethyl alcohol (100 ml) was added and the product was allowed to crystallize.

Filtration and washing with cold ethyl alcohol were done. Drying in oven at 40° C. in vacuum was then performed, obtaining 4.65 g.

m.p.=163°–167° C.

Calculated: C=42.44; H=6.65; N=13.20. Found: C=42.40; H=6.66; N=13.18.

HPLC assay=79.01% (GSEt); 20.99% (alanine)

EXAMPLE 6

GSEt aspartic acid salt (compound 6)

Equimolar quantities of GSEt (4.8 g) and of aspartic acid (1.90 g) were dissolved in $H_2O$ (200 ml) at room temperature. The solvent was evaporated to small volume, ethyl alcohol (100 ml) was added and the product was allowed to crystallize. Filtration and washing with cold ethyl alcohol were done. Drying in oven at 40° C. in vacuum was then performed, obtaining 5 g.

m.p.=135°–138° C.

Calculated: C=41.02; H=6.02; N=11.96. Found: C=41.00; H=6.03; N=11.95.

HPLC assay=71.59% (GSEt); 28.41% (aspartic acid)

EXAMPLE 7

GSEt glutamic acid salt (compound 7)

Equimolar quantities of GSEt (4.8 g) and of glutamic acid (2.10 g) were dissolved in $H_2O$ (100 ml) at 50° C. The solvent was evaporated to small voulume, ethyl alcohol (100 ml) was added and the product was allowed to crystallize.

Filtration and washing with cold ethyl alcohol were done. Drying in oven at 40° C. in vacuum was then performed, obtaining 5.1 g.

m.p.=187°–190° C.

Calculated: C=42.31; H=6.26; N=11.61. Found: C=42.29; H=6.25; N=11.63.

HPLC assay=69.51% (GSEt); 30.49% (glutamic acid)

EXAMPLE 8

GSIpr taurine salt (compound 8)

12.4 g of glutathione were suspended in 80 ml of isopropanol, 4.2 ml of $H_2SO_4$ 95% were added dropwise. The solution became clear. Stirring was continued overnight. Crystals began to separate and after 24 hours crystallization was finished. The solid was filtered off and washed with 20 ml of ice-cooled isopropanol. Crystals were dissolved in 150 ml of water and then purified charging it into a column packed with 25 ml of Amberlite IKC 68. The eluted fractions was added with an equimolar quantity of taurine then the solution was evaporated to dryness affording 15.3 g (80%) of title compound.

HPLC assay=72% (GSIpr); theoretical=73.63%; assay=97.9%.

EXAMPLE 9

GSIpr taurine salt (compound 8)

12.4 g of glutathione were suspended in 100 ml of isopropanol/hydrochloric acid 20%. The suspension became clear during 15 minutes. Stirring was continued overnight. The solvent was evaporated to dryness, 100 ml of water added and the pH was corrected to 8.5 with triethylamine. The mixture was extracted 6 times with 50 ml of $CH_2Cl_2$ each time. The organic layer was discarded. An equimolar amount of taurine was added to the water layer then the solution was evaporated to dryness to afford 15.5 g (81%) of the title compound.

HPLC assay=70% (GSIpr); theoretical=73.63%; assay=95%.

EXAMPLE 10

Ampoules for intravenous or intramuscular injection

Composition:

| | |
|---|---|
| Compound 2 | 30 mg |
| Sodium chloride FU IX | 30 mg |
| Water for injection | 5 ml |

Compound 2 was dissolved in 5 ml of water for injection, sodium chloride was added, filtration on 0.22μ membrane took place and the product was introduced in amber glass 5 ml ampoules. All operations were performed in a sterile environment.

EXAMPLE 11

Suppositories

Composition:

| | |
|---|---|
| Compound 6 | 200 mg |
| Witepsol H 15 Ph.Eur.to | 3 g |

A suspension of Compound 6 in melted Witepsol and, by the suitable machine, the 3 g suppository dies were filled. The whole was cooled.

EXAMPLE 12

Enteric-coated capsules

Composition:

| | |
|---|---|
| Compound 1 | 200 mg |
| Starch | 100 mg |
| Magnesium stearate | 2 mg |

The ingredients were mixed in a mixer and, by the suitable machine, they were shared into enteric-coated type 1 capsule.

EXAMPLE 13

Nasal spray

Composition:

| Compound 1 | 500 mg |
|---|---|
| Sodium chloride | 50 mg |
| Purified water | 10 ml |

Sodium chloride and compound 1 were dissolved in water, and the product was packaged in bottled equipped with 100 μl metering pump.

EXAMPLE 14

Enteric-coated tablets

Composition of core

| Compound 3 | 100 mg |
|---|---|
| Lactose | 60 mg |
| Starch | 40 mg |
| Aerosyl | 20 mg |
| Magnesium stearate | 2 mg |

Composition of coating

| Eudragit L | 3 mg |
|---|---|
| Eudragit S | 3 mg |

The mixture was compressed directly thus obtaining the cores, that were subsequently coated in a coating pan, by spraying the suspension of Eudragit L and Eudragit S in water.

We claim:

1. A crystalline non-hygroscopic salt of a glutathione alkylester of the formula (I)

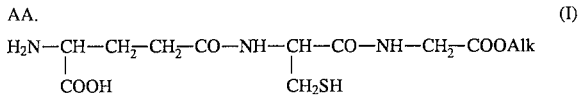

wherein AA is taurine and Alk is ethyl.

2. A pharmaceutical composition containing, as active ingredient, a compound of claim 1 in admixture with a pharmaceutical excipient.

3. A pharmaceutical composition according to claim 2, wherein the unit dosage of the active ingredient, calculated on the basis of the glutathione ester, is from 10 to 1000 mg.

4. A pharmaceutical composition according to claim 3, wherein the unit dosage of the active ingredient is from 20 to 500 mg.

* * * * *